(12) United States Patent
Kyperountas

(10) Patent No.: US 11,571,107 B2
(45) Date of Patent: Feb. 7, 2023

(54) AUTOMATED ENDOSCOPIC DEVICE CONTROL SYSTEMS

(71) Applicant: Karl Storz Imaging, Inc., Goleta, CA (US)

(72) Inventor: Marios Kyperountas, Goleta, CA (US)

(73) Assignee: KARL STORZ IMAGING, INC., Goleta, CA (US)

( * ) Notice: Subject to any disclaimer, the term of this patent is extended or adjusted under 35 U.S.C. 154(b) by 989 days.

(21) Appl. No.: 16/363,301

(22) Filed: Mar. 25, 2019

(65) Prior Publication Data
US 2020/0305682 A1   Oct. 1, 2020

(51) Int. Cl.
| | |
|---|---|
| A61B 1/00 | (2006.01) |
| G06N 3/02 | (2006.01) |
| A61B 90/00 | (2016.01) |
| G16H 20/40 | (2018.01) |
| A61B 34/20 | (2016.01) |
| A61B 1/06 | (2006.01) |

(52) U.S. Cl.
CPC ........ *A61B 1/00006* (2013.01); *A61B 1/0004* (2022.02); *A61B 1/000096* (2022.02); *A61B 90/361* (2016.02); *A61B 90/37* (2016.02); *G06N 3/02* (2013.01); *G16H 20/40* (2018.01); *A61B 1/0676* (2013.01); *A61B 34/20* (2016.02); *A61B 2090/0811* (2016.02)

(58) Field of Classification Search
CPC ............ A61B 1/00006; A61B 1/00009; A61B 90/361; A61B 90/37; A61B 1/0676; A61B 34/20; A61B 2090/0811; A61B 1/000096; G06N 3/02; G16H 20/40

See application file for complete search history.

(56) References Cited

U.S. PATENT DOCUMENTS

| | | | | |
|---|---|---|---|---|
| 5,368,015 | A  * | 11/1994 | Wilk ...................... | A61B 34/30 128/903 |
| 2010/0087798 | A1* | 4/2010 | Adams ................. | A61K 9/0034 604/515 |
| 2011/0125063 | A1 | 5/2011 | Shalon et al. | |
| 2012/0095458 | A1* | 4/2012 | Cybulski ............ | A61B 1/00183 606/41 |
| 2017/0042406 | A1* | 2/2017 | Naruse ..................... | A61B 5/06 |
| 2017/0079678 | A1* | 3/2017 | Ishikawa ................ | A61B 1/317 |

(Continued)

OTHER PUBLICATIONS

European Extended Search Report, EP App. 2016449.1, dated Aug. 10, 2020 (10 pages).

*Primary Examiner* — Anh Tuan T Nguyen
*Assistant Examiner* — Shankar Raj Ghimire
(74) *Attorney, Agent, or Firm* — Eversheds Sutherland (US) LLP

(57) ABSTRACT

Systems, methods, and computer-readable media are disclosed for automated endoscopic device control systems. In one embodiment, an example endoscopic device control system may include memory that stores computer-executable instructions, and at least one processor configured to access the memory and execute the computer-executable instructions to determine a first image from an endoscopic imaging system comprising a camera and a scope, determine, using the first image, that a first condition is present, determine a first response action to implement using a first endoscopic device, and automatically cause the first endoscopic device to implement the first response action.

10 Claims, 7 Drawing Sheets

(56) References Cited

U.S. PATENT DOCUMENTS

| | | | |
|---|---|---|---|
| 2018/0214005 A1* | 8/2018 | Ebata | A61B 5/0261 |
| 2018/0271615 A1 | 9/2018 | Mahadik et al. | |
| 2018/0296281 A1* | 10/2018 | Yeung | G06T 7/13 |
| 2019/0065970 A1 | 2/2019 | Bonutti et al. | |
| 2019/0336709 A1* | 11/2019 | Hong | A61B 5/01 |
| 2021/0165556 A1* | 6/2021 | Panse | G16H 40/63 |
| 2022/0071711 A1* | 3/2022 | Kyperountas | A61B 34/30 |
| 2022/0160430 A1* | 5/2022 | Landon | A61F 2/4609 |

* cited by examiner

AUTOMATED ENDOSCOPIC DEVICE CONTROL SYSTEMS

BACKGROUND

Certain medical procedures, such as endoscopies and the like, may be performed using medical equipment, such as endoscopes. Operators, such as physicians, assistants, and others may control medical equipment using manual controls, such as electronic or mechanical manual controls. However, during some medical procedures, certain changes may be made, or certain operations may be manually performed, to medical equipment by operators. For example, display settings may be adjusted, certain tools may be activated, and so forth. Such actions may be time consuming and/or involve more than one operator. Automated control systems may therefore be desired.

Figure 1:
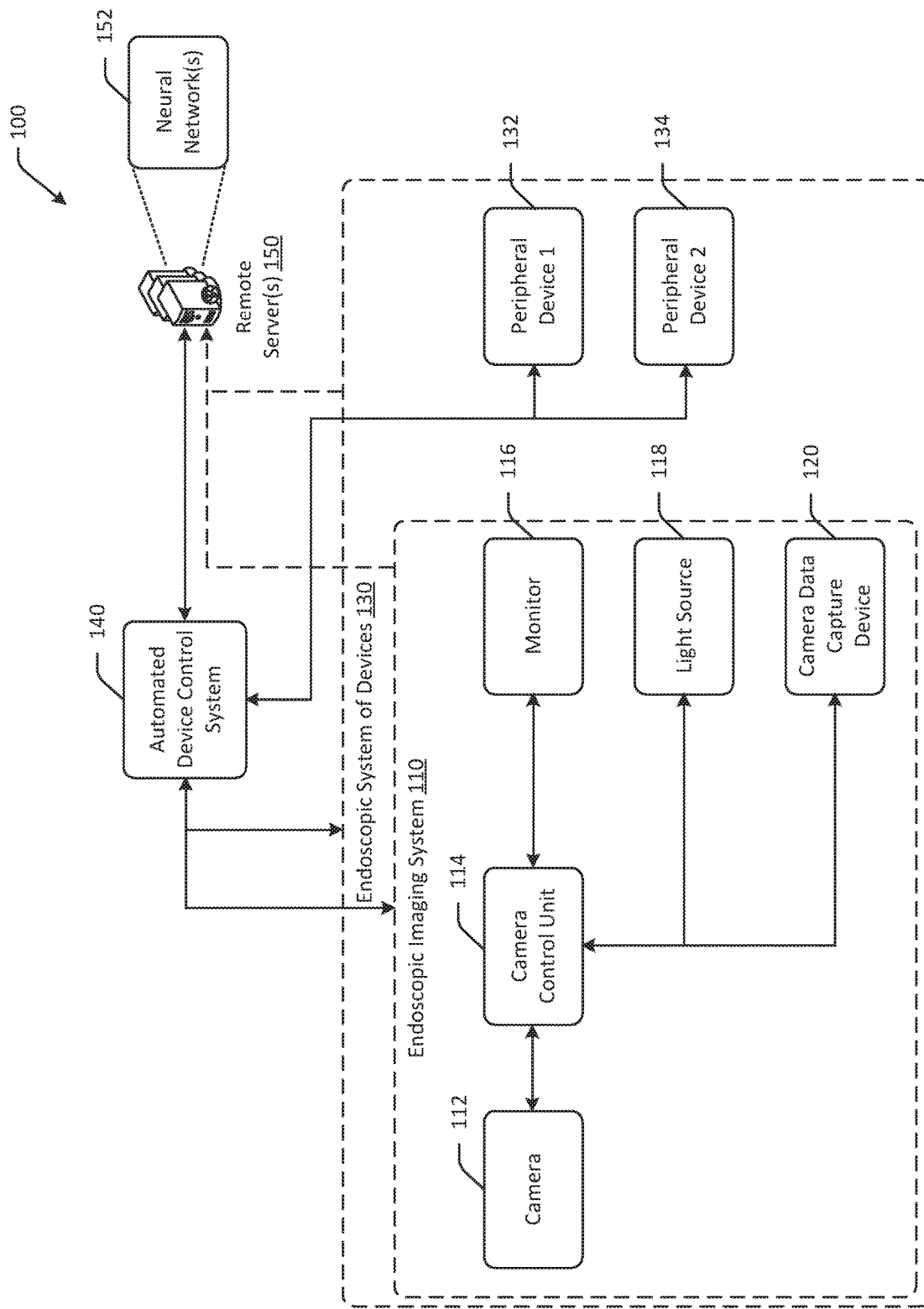
FIG. 1 is a system diagram illustrating an automated endoscopic device control system in accordance with one or more embodiments of the disclosure.

The detailed description is set forth with reference to the accompanying drawings. The drawings are provided for purposes of illustration only and merely depict example embodiments of the disclosure. The drawings are provided to facilitate understanding of the disclosure and shall not be deemed to limit the breadth, scope, or applicability of the disclosure. The use of the same reference numerals indicates similar but not necessarily the same or identical components; different reference numerals may be used to identify similar components as well. Various embodiments may utilize elements or components other than those illustrated in the drawings, and some elements and/or components may not be present in various embodiments. The use of singular terminology to describe a component or element may, depending on the context, encompass a plural number of such components or elements and vice versa.

SUMMARY

In an embodiment, an endoscopic device control system may include memory that stores computer-executable instructions, and at least one processor configured to access the memory and execute the computer-executable instructions to perform operations that may include determining a first image from an endoscopic imaging system comprising a camera and a scope, determining, using the first image, that a first condition is present, determining a first response action to implement using a first endoscopic device, and automatically causing the first endoscopic device to implement the first response action.

In another embodiment, an example method may include determining, by an endoscopic device control system, a first image from an endoscopic imaging system comprising a camera and a scope; determining, using the first image, that a first condition is present; determining a first response action to implement using a first endoscopic device; and automatically causing the first endoscopic device to implement the first response action.

In another embodiment, an example endoscopic device control system may be in communication with an endoscopic imaging system, a data collection system, and a first endoscopic device. The endoscopic device control system may include memory that stores computer-executable instructions, and at least one processor configured to access the memory and execute the computer-executable instructions to determine a first image from the endoscopic imaging system, determine, using the first image, that a first condition is present, determine a first response action to implement using the first endoscopic device, and automatically cause the first endoscopic device to implement the first response action.

DETAILED DESCRIPTION

Overview

Certain medical devices and equipment may be operated manually during medical procedures. For example, physicians, assistants, and/or others may operate medical equipment during a medical procedure. Manual control can increase the duration of medical procedures. For example, manual system configuration and/or modification, such as device settings modifications, may consume significant amounts of time from an operator. In addition, manual control can result in incorrect configuration of systems, in the event of operator error.

Embodiments of the disclosure include automated endoscopic device control systems that are configured to automatically perform certain actions based at least in part on one or more detected inputs. Certain embodiments may be configured to control camera systems (e.g., camera heads, integrated rigid and flexible scopes, etc.), camera control units, light sources, pumps, insufflators, monitors, lasers, robotic arms, data capture devices, and/or other devices that are manually controlled. Some embodiments may control devices using wired or wireless electronic communication.

Referring to FIG. 1, an example automated endoscopic device control system 100 is depicted in accordance with one or more embodiments of the disclosure. The automated endoscopic device control system 100 may include an endoscopic system of devices 130, an automated device control system 140, and/or one or more remote servers 150. The automated device control system 140 may be stored at a local computer system, such as a computer system in an operating room, or at one or more remote servers or computer systems. The remote server 150 may include or otherwise be configured to execute one or more neural networks 152. The neural network 152 may be used to process image and/or video data and manual action data to determine correlations between image data and manual actions. The neural network 152 may include a predictive model configured to generate automated actions or recommendations. In some embodiments, the neural network 152 may be stored at one or more servers and may be executed across a number of server or computer processors. The neural network 152 may implement machine learning and may be any suitable neural network framework, and may include one or more probabilistic and/or predictive models (e.g., TensorFlow, PyTorch, Caffe, etc.).

The endoscopic system of devices 130 may include an endoscopic imaging system 110. The endoscopic imaging system 110 may include one or more cameras 112, one or more camera control units 114, one or more monitors 116, one or more light sources 118, and/or one or more camera data capture devices 120. The endoscopic imaging system 110 may be used to capture images and/or carry tools to perform operations during an endoscopic procedure. The camera control unit 114 may be configured to control operation of the camera 112 and/or a scope coupled to the camera 112. The monitor 116 may display images or video captured by the camera 112. The light source 118 may provide lighting to illuminate a field of view of the camera 112. The camera data capture device 120 may be a computer system configured to record or otherwise capture data associated with the camera 112 and/or other components of the endoscopic imaging system 110.

The camera control unit 114 may be in electrical communication with the camera 112. For example, the camera control unit 114 may receive or otherwise determine learning data from the camera 112, the monitor 116, the light source 118, and/or the camera capture device 120. The learning data may include signals corresponding to manual actions performed at the respective devices. For example, learning data from the light source 118 may include times at which the light source 118 was activated or an amount by which a brightness setting was modified, etc. Learning data from the monitor 116 may include times and amounts of changes to monitor settings, and so forth. The camera control unit 114 may send learned control signals to one or more of the camera 112, the monitor 116, the light source 118, and/or the camera capture device 120. Learned control signals may include signals that cause the respective devices to perform certain actions. The camera control unit 114 may therefore cause other components or devices to implement certain actions.

The endoscopic system of devices 130 may include one or more peripheral devices, such as a first peripheral device 132, which may be an insufflator, and a second peripheral device 134, which may be a laser. Any number of peripheral devices may be included.

The endoscopic system of devices 130 may be in wired or wireless communication with the automated device control system 140. In some embodiments, the automated device control system 140 may be in direct communication with the endoscopic imaging system 110, while in other embodiments the automated device control system 140 may be in indirect communication with the endoscopic imaging system 110 via a wired or wireless connection with the endoscopic system of devices 130. The automated device control system 140 may be in direct or indirect wired or wireless communication with the first peripheral device 132 and/or the second peripheral device 134. The automated device control system 140 may receive learning data from the first peripheral device 132 and/or the second peripheral device 134, and may send learned control signals to the first peripheral device 132 and/or the second peripheral device 134.

The automated device control system 140 may be in wired or wireless communication with the remote server 150. The remote server may be a cloud-based data server and may process some or all of the learned data and/or control signals. The automated device control system 140 may be configured to employ recurrent neural networks in some embodiments.

In some instances, the endoscopic imaging system 110 and/or the endoscopic system of devices 130 may be in direct communication with the remote server 150. As a result, in some embodiments, the automated device control system 140 may receive learning data from, and control, one or more devices in the endoscopic imaging system 110 via the camera control unit 114. The automated device control system 140 may also receive learning data from, and control, one or more peripheral devices within the endoscopic system of devices 130 directly. The automated device control system 140 can process the learning data locally to generate a trained model. Optionally, the automated device control system 140 can send learning data to the remote server 150 that can then be processed, for example using recurrent neural networks, and a trained model can be downloaded by the automated device control system 140.

In another embodiment, the camera control unit 114 may receive learning data from one or more devices in the endoscopic imaging system 110, and may send the learning data (along with its own learning data) to the remote server 150 directly. Peripheral devices in the endoscopic system of devices 130 may also send learning data to the remote server 150 directly. The automated device control system 140 may download a trained model from the remote server periodically or whenever learning data is processed and an updated trained model is available. The devices in the endoscopic system of devices 130 may be controlled by signals generated by the automated device control system 140. For the endoscopic imaging system 110 devices, the control signals may be sent via the camera control unit 114. In some embodiments, the automated device control system 140 may receive learning data from all other devices in the endoscopic system of devices 130 directly.

Some embodiments may implement neural networks and/or machine learning to generate automated actions or recommendations. For example, the camera control unit 114 may be used to collect learning data during manual operation, which may be processed to teach the automated device control system 140 how to automatically control various devices. Training the automated device control system 140 may occur online (e.g., while the devices are in use manually, etc.) and/or offline. Using machine learning methods, such as deep learning with multi-layer neural networks, the collected learning data may be processed and used to generate a trained model that can be executed at the automated device control system 140. The automated device control system 140 may therefore control devices in the endoscopic system of devices 130. Offline and online qualification of the automated device control system 140 and/or trained models may be performed to determine when automated control and which parts of automated control can be enabled. Accordingly, certain embodiments may include artificial intelligence systems that use machine learning to automatically control and/or configure a system of devices for various tasks, such as instrument control, light source control, camera brightness control, navigation, data capture, etc. Such tasks may be performed automatically and faster relative to manual user control.

The automated device control system 140 may collect learning data and create, or update, a training model while the endoscopic system of devices 130 is manually being operated in the field to perform surgical procedures, and over time and multiple surgical procedures. The automated device control system 140 can be qualified online using a built-in qualification mechanism that may allow the automated device control system 140 to exercise control over one or more of the endoscopic system of devices 130. Optionally, a local or remote qualification mechanism can be used, by establishing a local or a remote connection.

In another embodiment, the automated device control system 140 may be trained offline using learning data collected from previous manual operations of the endoscopic system of devices 130 when performing surgical procedures. The automated device control system 140 may also be qualified offline using a qualification mechanism. The automated device configuration and control operations of the automated device control system 140 can be qualified and enabled by the qualification mechanism, either fully or partially. Indicators can be used to alert a user that the automated device control system 140 control functionality will become enabled. The user can be provided with the option to override or disable the automated device control system 140 control functionality to assume manual control. The automated device control system 140 may allow for user intervention with selecting the set of learning/training data it uses to produce its training model. The user can force the automated device control system 140 to disregard learning/training data collected from an unsuccessful or inefficient surgical procedure, or phase of such procedure.

In some instances, the automated device control system 140 can communicate directly with each device in the endoscopic system of devices 130, to receive learning data and to send learned control signals to the respective devices. In other instances, the automated device control system 140 may establish indirect communication and control of the endoscopic imaging system 110 devices through the camera control unit 114, which in turn may establish communication and control of the remaining devices in the endoscopic imaging system 110. The automated device control system 140 can also concurrently communicate with and control peripheral devices outside the endoscopic imaging system 110 and within the endoscopic system of devices 130. Such peripheral devices include but are not limited to insufflators, lasers, and robotic arms. The automated device control system 140 can be a local (e.g., within an operating room, within a hospital, etc.) device with established data communication and control of other local devices, or may be a local device with established data communication and control of both local and remote devices. In some instances, the automated device control system 140 can be a remote device with established data communication and control of local devices remotely. The automated device control system 140 can use both wired and wireless connections to the devices. In some instances, the endoscopic device control system 140 is configured to wirelessly communicate with the endoscopic imaging system 110.

The neural network 152 may receive one or more inputs that may be used to train and/or operate the neural network 152. For example, a first input may be learning data from the endoscopic imaging system 110. The neural network 152 may be configured to output one or more trained models that can be executed by the automated device control system 140 to generate real-time automated actions and/or recommendations for actions during endoscopic procedures. For example, using the trained model, the automated device control system 140 may determine that smoke is present within the field of view of the camera 112, and may generate an automated action of activating a suction or smoke reduction tool to remove the smoke automatically. To implement the action, the automated device control system 140 may send one or more control signals to the endoscopic system of devices 130 and/or to a particular peripheral device. In some embodiments, the trained model may be a predictive model that generates automated actions based at least in part on camera data received from the camera 112 and/or the camera control unit 114.

The automated device control system 140 may therefore learn and automatically configure and/or control one or more devices in the endoscopic imaging system 110 and, optionally, the endoscopic system of devices 130. The automated device control system 140 may learn to control devices by processing the learning data collected over time, and over multiple surgical procedures, from one or more devices during manual operation of the endoscopic system devices by operators. Qualification mechanisms may be used to confirm that automated actions are safe and effective. The automated device control system 140 may continuously learn over time and over multiple surgical procedures as new learning data become available, so as to improve the quality of automated actions and recommendations. In some instances, the automated device control system 140 may be partially enabled, or entirely disabled, until certain qualification metrics are satisfied. The automated device control system 140 may generate alerts to inform users of which devices and features and tasks are under or are about to come under automated control. Some or all automated tasks may be overridden by manual control. Learning data may be manually selected in some embodiments. Some embodiments may use a deep learning algorithm and/or deep (multi-layer) neural network to train and update models over time.

In some embodiments, the automated device control system 140 may be implemented as a local device that communicates with one or more local devices within the endoscopic system of devices 130, as well as one or more remote (e.g., outside the operating room and/or hospital, etc.) devices, such as the remote server 150. The automated device control system 140 may be implemented as a remote device that communicates with one or more local devices within the endoscopic system of devices 140, as well as one or more remote devices, such as the remote server 150. In some instances, the automated device control system 140 can control one or more devices within the endoscopic imaging system 110 and, optionally, other peripheral devices within the endoscopic system of devices 130, through the camera control unit 114. The automated device control system 140 can receive learning data from one or more devices within the endoscopic imaging system 110 and, optionally, other peripheral devices within the endoscopic system of devices 130, through the camera control unit 114.

In some embodiments, the automated device control system 140 may be integrated within the camera control unit 114. The automated device control system 140 may control devices within the endoscopic imaging system 110 and other peripheral devices within the endoscopic system of devices 130, directly, by establishing direct wired and/or wireless communication. The automated device control system 140 can receive learning data from one or more devices within the endoscopic imaging system 110 and from one or more peripheral devices within the endoscopic system of devices 130 directly, by establishing direct wired and/or wireless communication. The automated device control system 140 can be trained by sending the collected learning data to the remote server 150 that may employ various machine learning methods to generate a trained model. The trained model may be downloaded from the remote server 150 to the automated device control system 140. Optionally, the learning data can be sent directly to the remote server 150 from the one or more devices within the endoscopic imaging system 110 and one or more peripheral devices within the endoscopic system of devices 130, by establishing direct wireless communication. The automated device control system 140 can automatically configure parameters of the devices within the endoscopic imaging system 110 and of peripheral devices within the endoscopic system of devices 130. Parameters include enabling and/or disabling signals for automated control. The automated device control system 140 can automatically initiate a data capture process that can be used for documentation purposes and off-line diagnosis. The automated device control system 140 can be used to learn and then control the navigation of endoscopic instruments within and outside the human body. The automated device control system 140 can be used to learn to diagnose specified diseases and then control the endoscopic system of devices 130 to take action or execute a procedure (e.g., take a biopsy, etc.) based on the diagnosis. In addition, the automated device control system 140 may alert a user if the diagnosis is weak or whenever there is a need for the user to assume manual control. The automated device control system 140 may execute an automated task in a defined use case, including therapeutic tasks and diagnostic tasks. The automated device control system 140 may control robotic devices to collect and arrange equipment and devices, as needed for a specific type of medical procedure and for a specific phase of a medical procedure.

One or more illustrative embodiments of the disclosure have been described above. The above-described embodiments are merely illustrative of the scope of this disclosure and are not intended to be limiting in any way. Accordingly, variations, modifications, and equivalents of embodiments disclosed herein are also within the scope of this disclosure. The above-described embodiments and additional and/or alternative embodiments of the disclosure will be described in detail hereinafter through reference to the accompanying drawings.

Illustrative Processes and Use Cases

Figure 2:
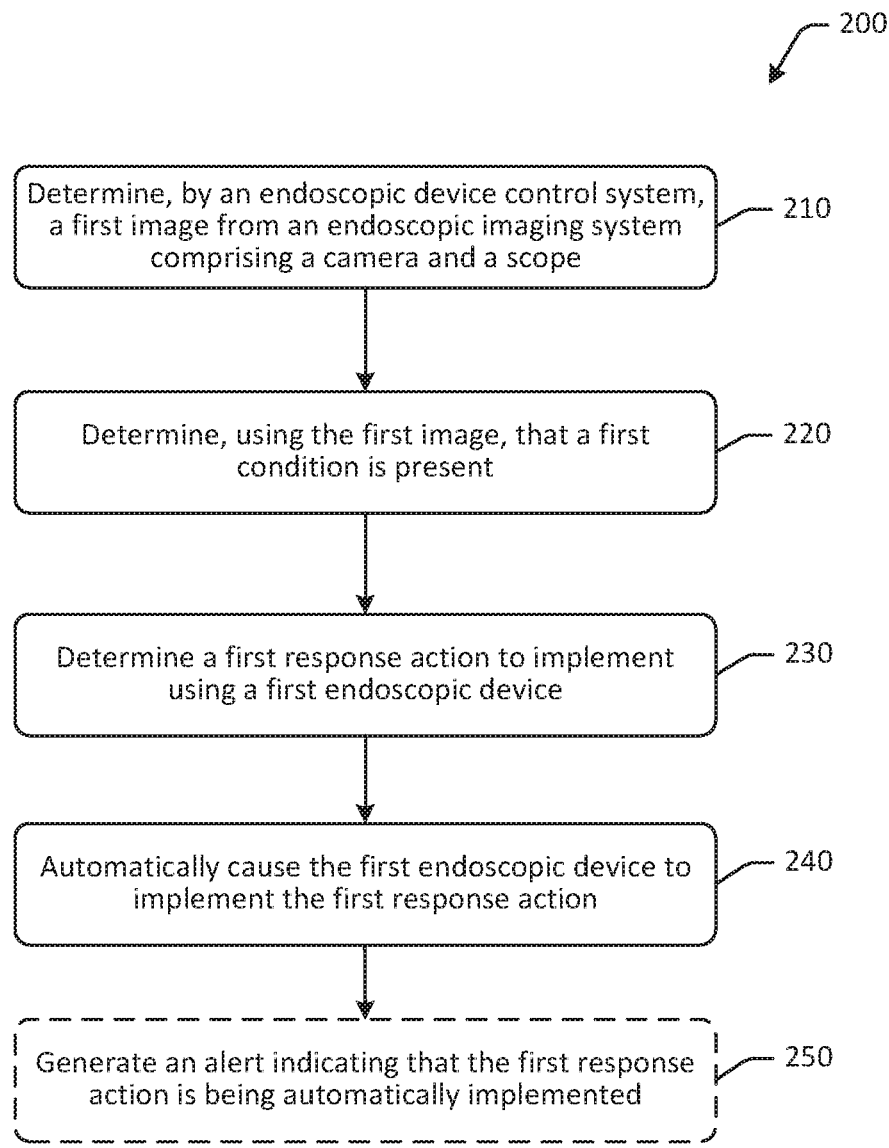
FIG. 2 is an example process flow diagram for automating endoscopic device actions in accordance with one or more embodiments of the disclosure.

Referring to FIG. 2, an example process flow 200 for automated endoscopic device control systems in accordance with one or more embodiments of the disclosure is depicted. Although certain operations are illustrated as occurring separately in FIG. 2, some or all of the operations may occur concurrently or partially concurrently across one or more computer systems. One or more operations may be optional in FIG. 2. The process flow 200 may be used, for example, to generate and/or train one or more neural networks and to automatically implement certain actions.

At block 210 of the process flow 200, an endoscopic device control system, such as the automated device control system 140 of FIG. 1, may determine a first image from an endoscopic imaging system, such as the endoscopic imaging system 110 of FIG. 1. For example, the endoscopic device control system may receive a first image from the endoscopic imaging system. The endoscopic imaging system may include a camera and/or a scope. The image may be captured using the camera. In some instances, the image may be determined from a video feed output by the camera.

At block 220 of the process flow 200, a first condition may be determined to be present using the first image. For example, the endoscopic device control system may process the first image and/or send the first image to a remote server for processing to determine whether any conditions are present. In some instances, portions of a video feed may be used to determine the presence of conditions. The first image may be processed using one or more pattern recognition algorithms and/or a trained model configured to determine a likelihood that a condition is present using computer vision. For example, based at least in part on output from one or more neural networks, a condition of smoke presence may be detected, or a condition corresponding to a biopsy recommendation may be detected. Any suitable condition may be detected. Various trained models may be configured to detect different conditions and/or different amounts of conditions, which may be based at least in part on data used to train the model. In addition to a detected condition, the model may output a confidence score indicative of a likelihood that the condition exists. For example, the higher the confidence score, the greater the likelihood that the condition exists. In some instances, the confidence score may be used to determine whether to implement an automatic action, such as activate a smoke reduction tool or other suction device.

At block 230 of the process flow 200, a first response action to implement using a first endoscopic device may be determined. For example, the endoscopic device control system may determine a response action that corresponds to the detected condition using the trained model and/or a remote server may determine a response action that corresponds to the detected condition by executing one or more neural networks. Based at least in part on learning data used to train the trained model, the endoscopic device control system may determine that a first response action is to adjust a camera setting, adjust a display brightness, activate a certain endoscopic device, such as a peripheral device (e.g., laser, insufflator, scope, etc.), and so forth. For example, the endoscopic device control system may determine that a first response action to implement is to activate a suction device responsive to a detected condition of smoke detection.

At block 240 of the process flow 200, the first endoscopic device may be automatically caused to implement the first response action. For example, the endoscopic device control system and/or a remote server may generate one or more command signals or otherwise instruct the first endoscopic device to implement the first response action. In some embodiments, the first response action may be directly implemented by the first endoscopic device, while in other embodiments, instructions to implement the first response action may be sent to a local device, such as a camera control unit, which may cause the first endoscopic device to automatically implement the first response action.

At optional block 250 of the process flow 200, an alert indicating that the first response action is being automatically implemented may be generated. For example, the endoscopic device control system and/or the first endoscopic device may generate an audible and/or visual alert that the first response action is being implemented, so as to alert an operator. As a result, the operator may allow the first response action to be implemented, or may cancel or otherwise override the automated action.

Accordingly, certain embodiments may detect conditions and automatically implement response action based at least in part on learning data used to train one or more predictive models or neural networks. As a result, time spent during procedures may be reduced, accuracy of actions may be improved, and consistency may be increased.

Examples of automated actions include, but are not limited to, detecting a smoke condition. For example, the endoscopic device control system may determine, using the first image, that an amount of smoke is greater than or equal to a smoke reduction threshold. The endoscopic device control system may therefore determine that a first endoscopic device, such as a smoke reduction device, is to be automatically activated. After the smoke reduction device is activated, the endoscopic device control system may determine a second image from the endoscopic imaging system, and may determine, using the second image, that the amount of smoke is less than the smoke reduction threshold. The endoscopic device control system may therefore automatically cancel the first response action, or may deactivate the smoke reduction device. Accordingly, the endoscopic device control system may use real-time or near real-time determinations to activate and/or deactivate endoscopic devices.

In another example, the endoscopic device control system may determine, using at least the first image, that a first endoscopic device of a camera controller is to adjust a brightness setting of a camera from a first value to a second value, where the brightness setting of the camera is controlled by the camera controller. The endoscopic device control system may therefore automatically adjust camera brightness based at least in part on image or video data.

In another example, the endoscopic device control system may determine, using at least the first image, that a first endoscopic device of a biopsy device is to extract a tissue sample. For example, the endoscopic device control system may determine, using at least the first image, coordinates for a tissue sample that is to be extracted, and may cause the biopsy device to extract the tissue sample using the coordinates. The endoscopic device control system may determine, using a second image, that the extraction is complete.

Figure 3:
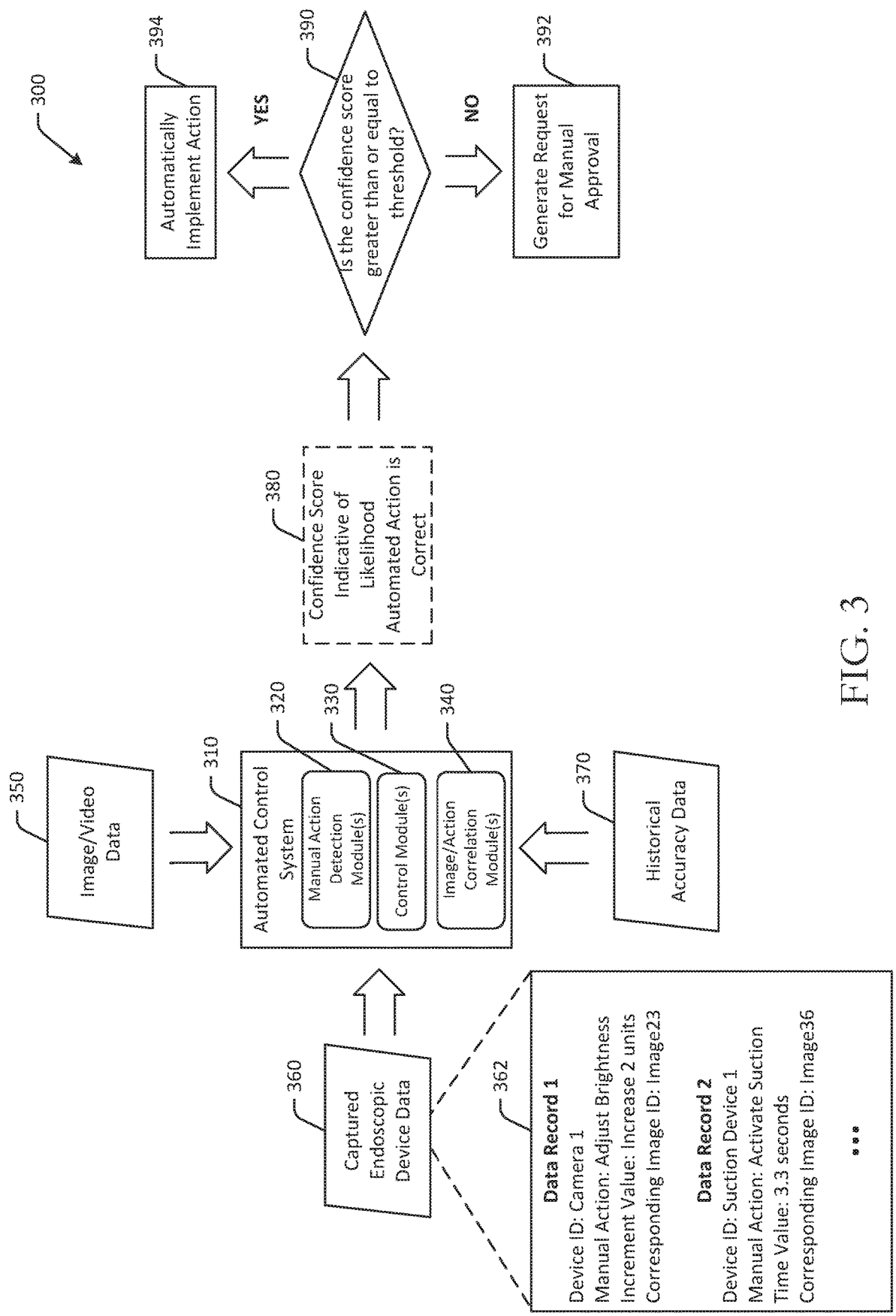
FIG. 3 depicts an example hybrid process and data flow in accordance with one or more embodiments of the disclosure.

FIG. 3 depicts an example hybrid process and data flow 300 in accordance with one or more embodiments of the disclosure. In some embodiments, one or more neural networks may be used to generate one or more automated actions or actions recommendations.

In FIG. 3, an automated control system 310 may be configured to automatically implement one or more actions at one or more endoscopic devices. The automated control system 310 may be local at an operating room, or may be a remote device, such as at a remote server. In some embodiments, the automated control system 310 may be integrated into a control unit of an endoscopic system of devices.

The automated control system 310 may include one or more manual action detection modules 320 configured to detect manual actions for learning data, one or more control modules 330 configured to implement automatic actions at endoscopic devices, and one or more image/action correlation modules 340 configured to generate automated actions and optional confidence scores.

The automated control system 310 may use one or more inputs to generate outputs of automated actions and/or confidence scores. For example, a first input of image/video data 350 may include live video or image feeds from, for example, a camera during a procedure. The image/video data input 350 may be processed by the automated control system 310 to determine whether any conditions are present.

A second input of captured endoscopic device data 360 may include data records 362 of previous manual actions performed using specific devices and corresponding images. The automated control system 310 may process the captured endoscopic device data 360 to learn which actions are performed at which times using which endoscopic devices, as well as the corresponding image or videos. For example, the captured endoscopic device data may indicate that a camera brightness was adjusted at a time image 23 was captured, which may be used to associate a condition present at the time the brightness was adjusted. For example, the automated control system 310 may process the image 23 to determine the condition that was present at the time the brightness was manually adjusted. Another data record may indicate that the suction device was activated for 3.3 seconds at a time image 36 was captured, and so forth.

A third input of historical accuracy data 370 may be used by the automated control system 310 to determine confidence scores. The historical accuracy data 370 may indicate how many automated actions were overridden by manual control, how many automated actions were approved or otherwise not overridden, and so forth. The automated control system 310 may use the historical accuracy data 370 to improve confidence scores for subsequent automated actions.

In addition to an automated action or action recommendation (for execution by an operator), the automated control system 310 may output an optional confidence score 380 indicative of a likelihood that an automated action is correct. The automated action or action recommendation, as well as the confidence score, may be generated based at least in part on the image/video data 350, the captured endoscopic device data 360 (which may be used to train a model that is used by the automated control system 310), and/or the historical accuracy data 370.

The automated control system 310 may make a determination at determination block 390 as to whether the confidence score is greater than or equal to a threshold. If the automated control system 310 determines at determination block 390 that the confidence score is not greater than or equal to the threshold, the automated control system 310 may generate a request for manual approval at block 392. If the automated control system 310 determines at determination block 390 that the confidence score is greater than or equal to the threshold, the automated control system 310 may automatically implement the action at block 394.

Figure 4:
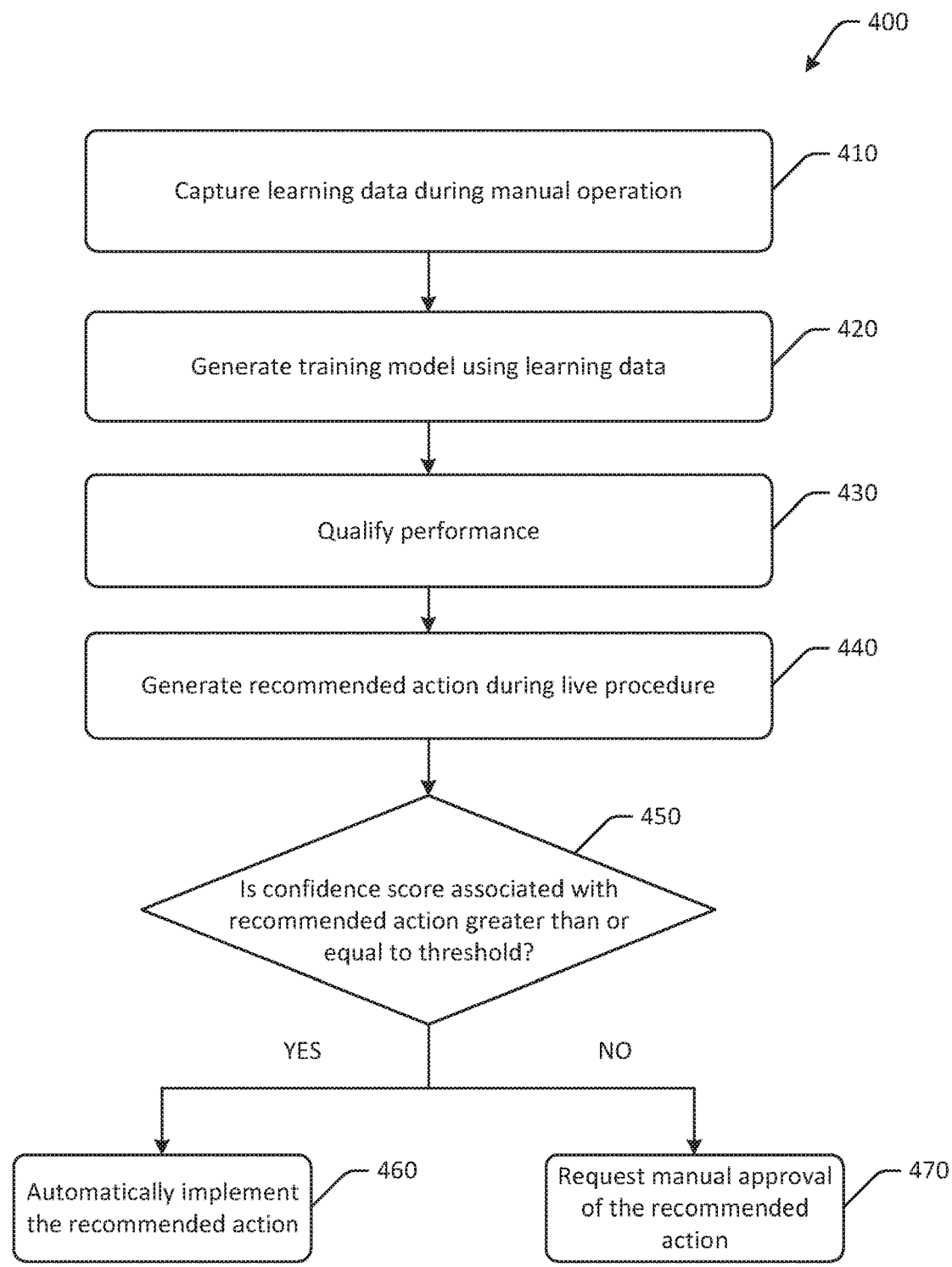
FIG. 4 is an example process flow diagram for determining automated actions in accordance with one or more embodiments of the disclosure.

FIG. 4 is an example process flow 400 for determining automated actions in accordance with one or more embodiments of the disclosure. The process flow 400 of FIG. 4 may be used, for example, to determine an automated action, and/or to determine whether to implement an automated action.

At block 410 of the process flow 400, learning data may be captured during manual operation of endoscopic devices. For example, an automated control system may determine a manual action performed using a first endoscopic device during a procedure. The automated control system may determine one or more parameters present at or near a time at which the manual action was performed. The automated control system may optionally send an indication of the manual action and the one or more parameters to a neural network as inputs for a training model. For example, a remote server may use the data captured by the automated control system as inputs to train a training model for use in generating automated actions.

At block 420, a training model may be generated using learning data. For example, the automated control system and/or remote server may generate a training model using the learning data. In some embodiments, neural networks may be used to generate a training model and/or implement a trained model.

At block 430, performance of the trained model may be qualified. Qualification may be performed by the automated control system and/or remote server, or with a third party device. Qualification may include manual review and/or qualification of automated control system performance. In some embodiments, confidence score thresholds may be used for qualification with respect to confidence scores associated with particular automated actions.

At block 440, a recommended action may be generated during a live procedure. For example, based at least in part on image and/or video data, a recommended action may be generated during a live procedure. For example, activation of a suction tool may be generated as a recommended action where smoke is detected in image or video data.

At determination block 450, a determination may be made as to whether a confidence score associated with the recommended action is greater than or equal to a threshold. For example, the automated control system may compare the confidence score to the threshold. If it is determined that the confidence score indicative of a likelihood that the first response action is a correct action is greater than or equal to the threshold, such as an automated action threshold, the process flow 400 may proceed to block 460, at which the recommended action may be automatically implemented. If it is determined that the confidence score indicative of a likelihood that the first response action is a correct action is less than the threshold, such as the automated action threshold, the process flow 400 may proceed to block 470, at which manual approval of the recommended action may be requested. For example, the automated control system may generate a recommendation notification for the first response action that includes a request for manual approval of the first response action. The recommendation notification may be presented at a display or other endoscopic device. If an indication of manual approval is received, the action may be implemented, and a confidence score model used to generate confidence scores may be updated based at least in part on the indication of manual approval.

Figure 5:
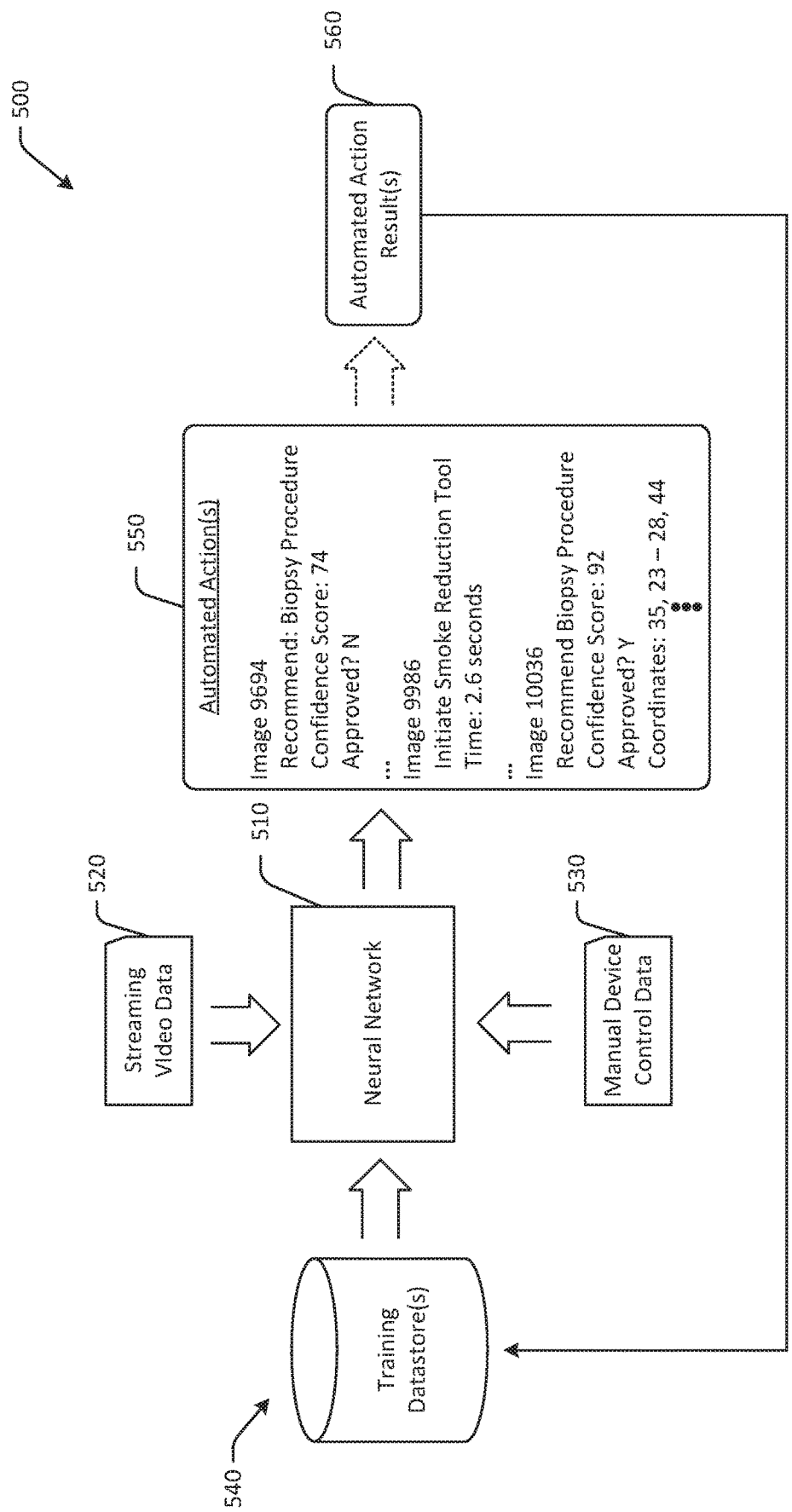
FIG. 5 depicts an example hybrid process and data flow in accordance with one or more embodiments of the disclosure.

FIG. 5 depicts an example hybrid system and process flow diagram 500 in accordance with one or more embodiments of the disclosure. In FIG. 5, a neural network 510 may include computer-executable instructions to generate automated actions for endoscopic procedures. The neural network 510 may receive streaming video data 520, manual device control data 530, and training datastore data 540. The neural network 510 may output automated actions 550 using the streaming video data 520, manual device control data 530, and training datastore data 540. For example, the neural network 510 may output, for one or more images, recommended actions, confidence scores, and indications of manual approval (as needed). For example, for image 9694, the neural network 510 may output a recommendation of a biopsy procedure with a confidence score of 74, and an indication that manual approval was not received. Another image 9986 may include an action of initiate smoke reduction tool for 2.6 seconds that satisfies a confidence score threshold and is therefore automatically implemented. Another image 10036 may be associated with a biopsy procedure recommendation and a confidence score of 92, and may be manually approved, and coordinates may be therefore be output for the biopsy procedure.

Automated action results 560 may include data gathered after automated actions are performed or actions are recommended, such as indications of manual approval or rejection, and may be fed to training datastore 540 to improve subsequent performance of the neural network 510.

Figure 6:
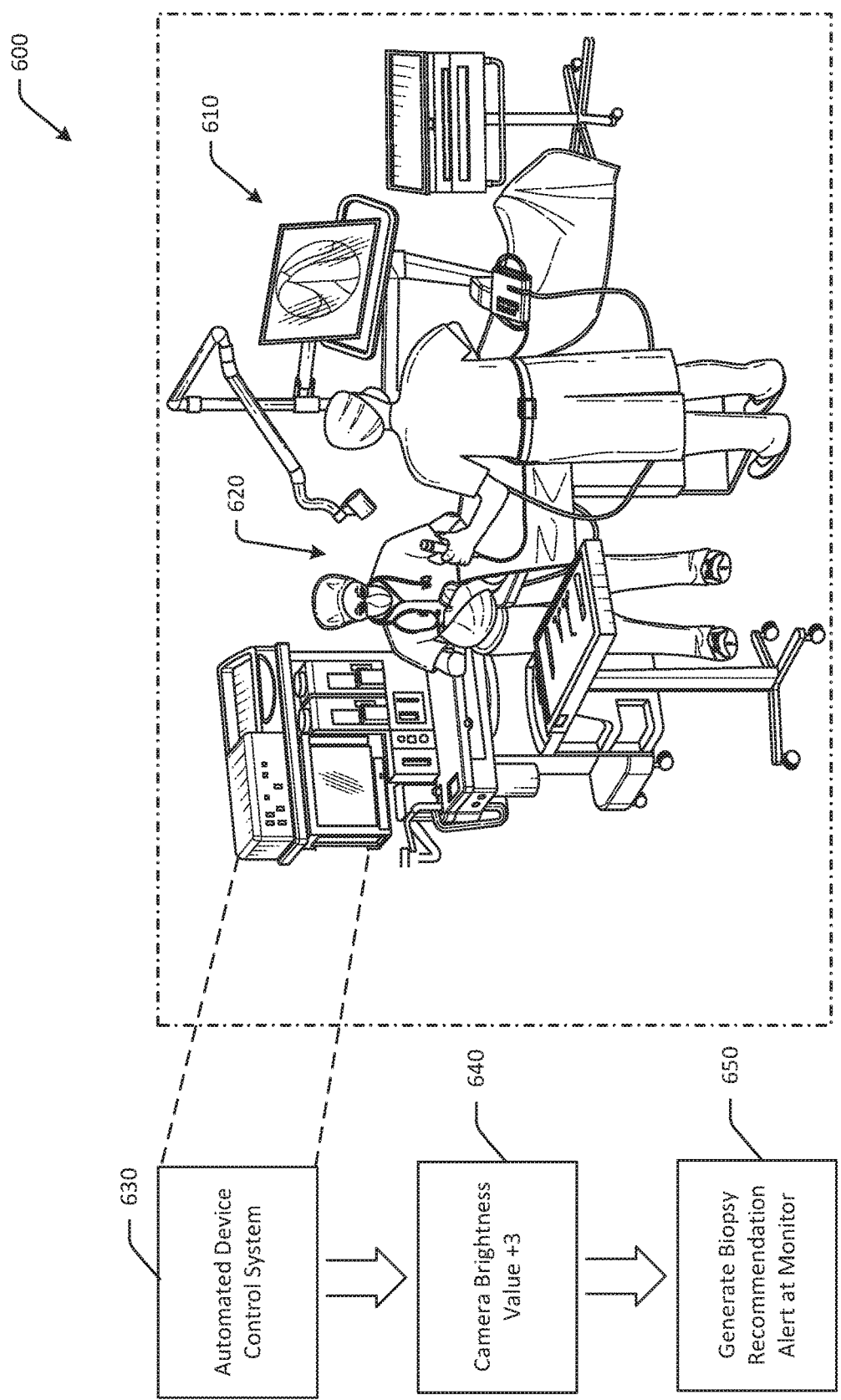
FIG. 6 is an example use case for automated endoscopic device control systems in accordance with one or more embodiments of the disclosure.

FIG. 6 depicts an example use case 600 for automated endoscopic device control systems in accordance with one or more embodiments of the disclosure. In FIG. 6, an endoscopic system of devices 610 may include a camera system 620. One or more neural networks may be used in conjunction with an automated device control system 630 to generate automated actions. For example, the automated device control system 630 may generate a first action 640 of increasing the camera brightness of the camera 620 by three points, a second action 650 of generating a biopsy recommendation alert at a monitor, and so forth over the course of a procedure.

One or more operations of the method, process flows, or use cases of FIGS. 1-6 may have been described above as being performed by a user device, or more specifically, by one or more program module(s), applications, or the like executing on a device. It should be appreciated, however, that any of the operations of methods, process flows, or use cases of FIGS. 1-6 may be performed, at least in part, in a distributed manner by one or more other devices, or more specifically, by one or more program module(s), applications, or the like executing on such devices. In addition, it should be appreciated that processing performed in response to execution of computer-executable instructions provided as part of an application, program module, or the like may be interchangeably described herein as being performed by the application or the program module itself or by a device on which the application, program module, or the like is executing. While the operations of the methods, process flows, or use cases of FIGS. 1-6 may be described in the context of the illustrative devices, it should be appreciated that such operations may be implemented in connection with numerous other device configurations.

The operations described and depicted in the illustrative methods, process flows, and use cases of FIGS. 1-6 may be carried out or performed in any suitable order, such as the depicted orders, as desired in various example embodiments of the disclosure. Additionally, in certain example embodiments, at least a portion of the operations may be carried out in parallel. Furthermore, in certain example embodiments, less, more, or different operations than those depicted in FIGS. 1-6 may be performed.

Although specific embodiments of the disclosure have been described, one of ordinary skill in the art will recognize that numerous other modifications and alternative embodiments are within the scope of the disclosure. For example, any of the functionality and/or processing capabilities described with respect to a particular device or component may be performed by any other device or component. Further, while various illustrative implementations and architectures have been described in accordance with embodiments of the disclosure, one of ordinary skill in the art will appreciate that numerous other modifications to the illustrative implementations and architectures described herein are also within the scope of this disclosure.

Certain aspects of the disclosure are described above with reference to block and flow diagrams of systems, methods, apparatuses, and/or computer program products according to example embodiments. It will be understood that one or more blocks of the block diagrams and flow diagrams, and combinations of blocks in the block diagrams and the flow diagrams, respectively, may be implemented by execution of computer-executable program instructions. Likewise, some blocks of the block diagrams and flow diagrams may not necessarily need to be performed in the order presented, or may not necessarily need to be performed at all, according to some embodiments. Further, additional components and/or operations beyond those depicted in blocks of the block and/or flow diagrams may be present in certain embodiments.

Accordingly, blocks of the block diagrams and flow diagrams support combinations of means for performing the specified functions, combinations of elements or steps for performing the specified functions, and program instruction means for performing the specified functions. It will also be understood that each block of the block diagrams and flow diagrams, and combinations of blocks in the block diagrams and flow diagrams, may be implemented by special-purpose, hardware-based computer systems that perform the specified functions, elements or steps, or combinations of special-purpose hardware and computer instructions.

Illustrative Computer Architecture

Figure 7:
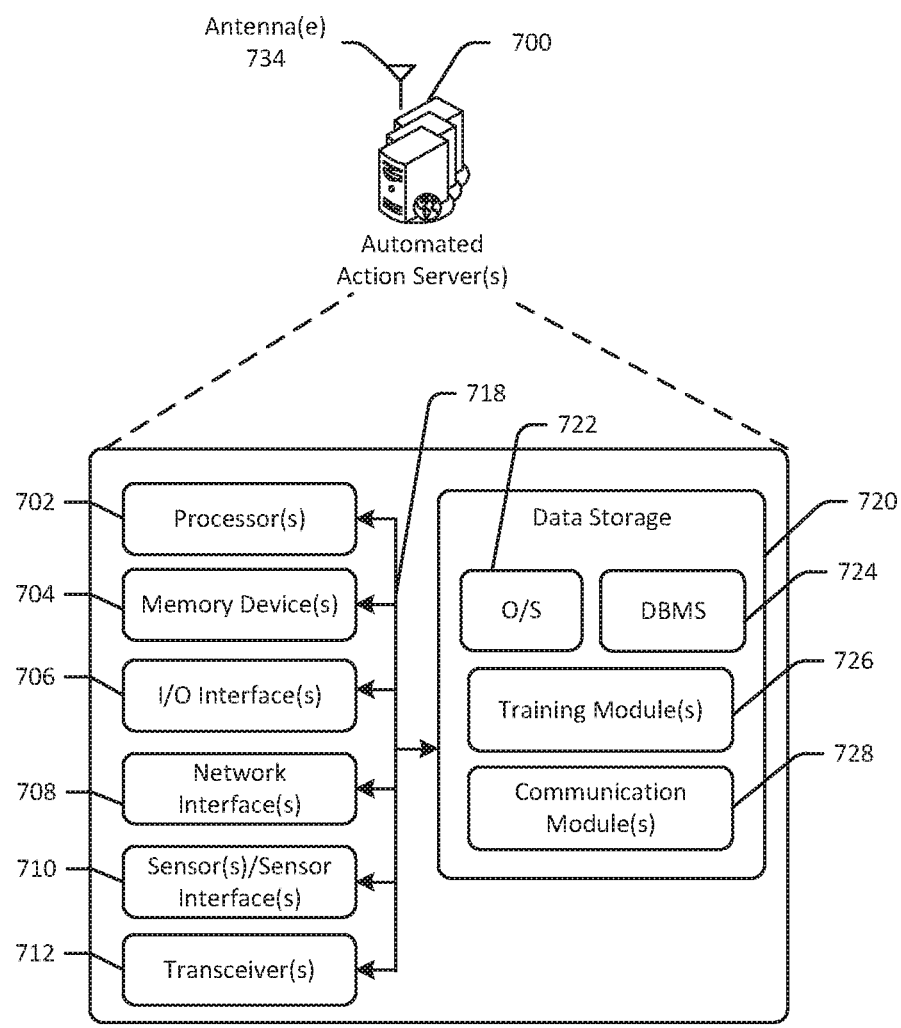
FIG. 7 schematically illustrates an example architecture of a neural network server in accordance with one or more embodiments of the disclosure.

FIG. 7 is a schematic block diagram of one or more illustrative automated action server(s) 700 in accordance with one or more example embodiments of the disclosure. The automated action server(s) 700 may include any suitable computing device including, but not limited to, a server system, an endoscopic device or system, a mobile device such as a smartphone, tablet, e-reader, wearable device, or the like; a desktop computer; a laptop computer; a content streaming device; a set-top box; or the like. The automated action server(s) 700 may correspond to an illustrative device configuration for the neural network servers or content selection servers of FIGS. 1-6.

The automated action server(s) 700 may be configured to communicate via one or more networks with one or more servers, user devices, or the like. The automated action server(s) 700 may be configured to process image and/or video data, generate automated actions, generate alerts, generate notifications, and other operations. The automated action server(s) 700 may be configured to train one or more neural networks. In some embodiments, a single remote server or single group of remote servers may be configured to perform more than one type of neural network related functionality.

In an illustrative configuration, the automated action server(s) 700 may include one or more processors (processor(s)) 702, one or more memory devices 704 (generically referred to herein as memory 704), one or more input/output (I/O) interfaces 706, one or more network interfaces 708, one or more sensors or sensor interfaces 710, one or more transceivers 712, and data storage 720. The automated action server(s) 700 may further include one or more buses 718 that functionally couple various components of the automated action server(s) 700. The automated action server(s) 700 may further include one or more antenna(e) 734 that may include, without limitation, a cellular antenna for transmitting or receiving signals to/from a cellular network infrastructure, an antenna for transmitting or receiving Wi-Fi signals to/from an access point (AP), a Global Navigation Satellite System (GNSS) antenna for receiving GNSS signals from a GNSS satellite, a Bluetooth antenna for transmitting or receiving Bluetooth signals, a Near Field Communication (NFC) antenna for transmitting or receiving NFC signals, and so forth. These various components will be described in more detail hereinafter.

The memory 704 of the automated action server(s) 700 may include volatile memory (memory that maintains its state when supplied with power) such as random access memory (RAM) and/or non-volatile memory (memory that maintains its state even when not supplied with power) such as read-only memory (ROM), flash memory, ferroelectric RAM (FRAM), and so forth. Persistent data storage, as that term is used herein, may include non-volatile memory. In certain example embodiments, volatile memory may enable faster read/write access than non-volatile memory. However, in certain other example embodiments, certain types of non-volatile memory (e.g., FRAM) may enable faster read/write access than certain types of volatile memory.

The data storage 720 may store one or more operating systems (O/S) 722; one or more database management systems (DBMS) 724; and one or more program module(s), applications, engines, computer-executable code, scripts, or the like such as, for example, one or more training module(s) 726, and one or more communication module(s) 728. Some or all of these module(s) may be sub-module(s). Any of the components depicted as being stored in data storage 720 may include any combination of software, firmware, and/or hardware. The software and/or firmware may include computer-executable code, instructions, or the like that may be loaded into the memory 704 for execution by one or more of the processor(s) 702. Any of the components depicted as being stored in data storage 720 may support functionality described in reference to correspondingly named components earlier in this disclosure.

The processor(s) 702 may be configured to access the memory 704 and execute computer-executable instructions loaded therein. For example, the processor(s) 702 may be configured to execute computer-executable instructions of the various program module(s), applications, engines, or the like of the automated action server(s) 700 to cause or facilitate various operations to be performed in accordance with one or more embodiments of the disclosure. The processor(s) 702 may include any suitable processing unit capable of accepting data as input, processing the input data in accordance with stored computer-executable instructions, and generating output data. The processor(s) 702 may include any type of suitable processing unit including, but not limited to, a central processing unit, a microprocessor, a Reduced Instruction Set Computer (RISC) microprocessor, a Complex Instruction Set Computer (CISC) microprocessor, a microcontroller, an Application Specific Integrated Circuit (ASIC), a Field-Programmable Gate Array (FPGA), a System-on-a-Chip (SoC), a digital signal processor (DSP), and so forth. Further, the processor(s) 702 may have any suitable microarchitecture design that includes any number of constituent components such as, for example, registers, multiplexers, arithmetic logic units, cache controllers for controlling read/write operations to cache memory, branch predictors, or the like. The microarchitecture design of the processor(s) 702 may be capable of supporting any of a variety of instruction sets.

Referring now to functionality supported by the various program module(s) depicted in FIG. 7, the training module(s) 726 may include computer-executable instructions, code, or the like that responsive to execution by one or more of the processor(s) 702 may perform functions including, but not limited to, generating or determining predictive models and/or probabilistic models, using or determining data sets, such as training data sets, determining inputs to or outputs of one or more neural networks, determining an accuracy of one or more neural networks, and the like.

The communication module(s) 728 may include computer-executable instructions, code, or the like that responsive to execution by one or more of the processor(s) 702 may perform functions including, but not limited to, communicating with remote servers, communicating with remote datastores, sending or receiving notifications, communicating with cache memory data, communicating with endoscopic devices, and the like.

Referring now to other illustrative components depicted as being stored in the data storage 720, the O/S 722 may be loaded from the data storage 720 into the memory 704 and may provide an interface between other application software executing on the automated action server(s) 700 and hardware resources of the automated action server(s) 700. More specifically, the O/S 722 may include a set of computer-executable instructions for managing hardware resources of the automated action server(s) 700 and for providing common services to other application programs (e.g., managing memory allocation among various application programs). In certain example embodiments, the O/S 722 may control execution of the other program module(s) to dynamically enhance characters for content rendering. The O/S 722 may include any operating system now known or which may be developed in the future including, but not limited to, any server operating system, any mainframe operating system, or any other proprietary or non-proprietary operating system.

The DBMS 724 may be loaded into the memory 704 and may support functionality for accessing, retrieving, storing, and/or manipulating data stored in the memory 704 and/or data stored in the data storage 720. The DBMS 724 may use any of a variety of database models (e.g., relational model, object model, etc.) and may support any of a variety of query languages. The DBMS 724 may access data represented in one or more data schemas and stored in any suitable data repository including, but not limited to, databases (e.g., relational, object-oriented, etc.), file systems, flat files, distributed datastores in which data is stored on more than one node of a computer network, peer-to-peer network datastores, or the like. In those example embodiments in which the automated action server(s) 700 is a mobile device, the DBMS 724 may be any suitable light-weight DBMS optimized for performance on a mobile device.

Referring now to other illustrative components of the automated action server(s) 700, the input/output (I/O) interface(s) 706 may facilitate the receipt of input information by the automated action server(s) 700 from one or more I/O devices as well as the output of information from the automated action server(s) 700 to the one or more I/O devices. The I/O devices may include any of a variety of components such as a display or display screen having a touch surface or touchscreen; an audio output device for producing sound, such as a speaker; an audio capture device, such as a microphone; an image and/or video capture device, such as a camera; a haptic unit; and so forth. Any of these components may be integrated into the automated action server(s) 700 or may be separate. The I/O devices may further include, for example, any number of peripheral devices such as data storage devices, printing devices, and so forth.

The automated action server(s) 700 may further include one or more network interface(s) 708 via which the automated action server(s) 700 may communicate with any of a variety of other systems, platforms, networks, devices, and so forth. The network interface(s) 708 may enable communication, for example, with one or more wireless routers, one or more host servers, one or more web servers, and the like via one or more of networks.

The antenna(e) 734 may include any suitable type of antenna depending, for example, on the communications protocols used to transmit or receive signals via the antenna (e) 734. Non-limiting examples of suitable antennas may include directional antennas, non-directional antennas, dipole antennas, folded dipole antennas, patch antennas, multiple-input multiple-output (MIMO) antennas, or the like. The antenna(e) 734 may be communicatively coupled to one or more transceivers 712 or radio components to which or from which signals may be transmitted or received.

The antenna(e) 734 may additionally, or alternatively, include a Wi-Fi antenna configured to transmit or receive signals in accordance with established standards and protocols, such as the IEEE 802.11 family of standards, including via 2.4 GHz channels (e.g., 802.11b, 802.11g, 802.11n), 5 GHz channels (e.g., 802.11n, 802.11ac), or 60 GHz channels (e.g., 802.11ad). In alternative example embodiments, the antenna(e) 734 may be configured to transmit or receive radio frequency signals within any suitable frequency range forming part of the unlicensed portion of the radio spectrum.

The transceiver(s) 712 may include any suitable radio component(s) for—in cooperation with the antenna(e) 734—transmitting or receiving radio frequency (RF) signals in the bandwidth and/or channels corresponding to the communications protocols utilized by the automated action server(s) 700 to communicate with other devices. The transceiver(s) 712 may include hardware, software, and/or firmware for modulating, transmitting, or receiving—potentially in cooperation with any of antenna(e) 734—communications signals according to any of the communications protocols discussed above including, but not limited to, one or more Wi-Fi and/or Wi-Fi direct protocols, as standardized by the IEEE 802.11 standards, one or more non-Wi-Fi protocols, or one or more cellular communications protocols or standards. The transceiver(s) 712 may further include hardware, firmware, or software for receiving GNSS signals. The transceiver(s) 712 may include any known receiver and baseband suitable for communicating via the communications protocols utilized by the automated action server(s) 700. The transceiver(s) 712 may further include a low noise amplifier (LNA), additional signal amplifiers, an analog-to-digital (A/D) converter, one or more buffers, a digital baseband, or the like.

The sensor(s)/sensor interface(s) 710 may include or may be capable of interfacing with any suitable type of sensing device such as, for example, inertial sensors, force sensors, thermal sensors, and so forth. Example types of inertial sensors may include accelerometers (e.g., MEMS-based accelerometers), gyroscopes, and so forth.

It should be appreciated that the automated action server(s) 700 may include alternate and/or additional hardware, software, or firmware components beyond those described or depicted without departing from the scope of the disclosure. More particularly, it should be appreciated that software, firmware, or hardware components depicted as forming part of the automated action server(s) 700 are merely illustrative and that some components may not be present or additional components may be provided in various embodiments. While various illustrative program module(s) have been depicted and described as software module(s) stored in data storage 720, it should be appreciated that functionality described as being supported by the program module(s) may be enabled by any combination of hardware, software, and/or firmware. It should further be appreciated that each of the above-mentioned module(s) may, in various embodiments, represent a logical partitioning of supported functionality. This logical partitioning is depicted for ease of explanation of the functionality and may not be representative of the structure of software, hardware, and/or firmware for implementing the functionality. Accordingly, it should be appreciated that functionality described as being provided by a particular module may, in various embodiments, be provided at least in part by one or more other module(s). Further, one or more depicted module(s) may not be present in certain embodiments, while in other embodiments, additional module(s) not depicted may be present and may support at least a portion of the described functionality and/or additional functionality. Moreover, while certain module(s) may be depicted and described as sub-module(s) of another module, in certain embodiments, such module(s) may be provided as independent module(s) or as sub-module(s) of other module(s).

Although embodiments have been described in language specific to structural features and/or methodological acts, it is to be understood that the disclosure is not necessarily limited to the specific features or acts described. Rather, the specific features and acts are disclosed as illustrative forms of implementing the embodiments. Conditional language, such as, among others, "can," "could," "might," or "may," unless specifically stated otherwise, or otherwise understood within the context as used, is generally intended to convey that certain embodiments could include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

That which is claimed is:

1. An endoscopic device control system comprising:
   a memory that is a non-transitory computer readable medium that stores computer-executable instructions; and
   at least one processor configured to access the memory and execute the computer-executable instructions to:
      determine a manual action performed using a first endoscopic device;
      determine one or more parameters present at or near a time at which the manual action was performed;
      send an indication of the manual action and the one or more parameters to a neural network as inputs for a training model;
      determine a first image from an endoscopic imaging system comprising a camera and a scope;
      determine, using the first image, that a first condition is present;
      determine a first response action to implement using the first endoscopic device;
      determine that a confidence score indicative of a likelihood that the first response action is a correct action is less than an automated action threshold;
      in response to determining the confidence score, generate a recommendation notification for the first response action comprising a request for manual approval of the first response action; and
      cause the first endoscopic device to implement the first response action.

2. The endoscopic device control system of claim 1, wherein the at least one processor is further configured to access the at least one memory and execute the computer-executable instructions to:
   automatically cancel the first response action.

3. The endoscopic device control system of claim 1, wherein the at least one processor is further configured to access the at least one memory and execute the computer-executable instructions to:
   automatically implement a second response action using a second endoscopic device.

4. The endoscopic device control system of claim 1, wherein the at least one processor is further configured to access the at least one memory and execute the computer-executable instructions to:
   determine that the first response action is complete; and
   cause the endoscopic device control system to resume a manual mode.

5. The endoscopic device control system of claim 1, wherein the at least one processor is further configured to access the at least one memory and execute the computer-executable instructions to:
   generate an alert indicating that the first response action is being automatically implemented.

6. The endoscopic device control system of claim 1, wherein the at least one processor is further configured to access the at least one memory and execute the computer-executable instructions to:
   initiate a training operation to update the training model using the indication of the manual action.

7. The endoscopic device control system of claim 1, wherein the at least one processor is further configured to access the at least one memory and execute the computer-executable instructions to:
   determine that a confidence score indicative of a likelihood that the first response action is a correct action is greater than or equal to an automated action threshold.

8. The endoscopic device control system of claim 1, wherein the at least one processor is further configured to access the at least one memory and execute the computer-executable instructions to:
   receive an indication of manual approval; and
   update, based at least in part on the indication of manual approval, a confidence score model.

9. The endoscopic device control system of claim 1, wherein the endoscopic device control system is configured to wirelessly communicate with the endoscopic imaging system.

10. An endoscopic device control system in communication with an endoscopic imaging system, a data collection system, and a first endoscopic device, the endoscopic device control system comprising:
   a memory that is a non-transitory computer readable medium that stores computer- executable instructions; and
   at least one processor configured to access the memory and execute the computer- executable instructions to:
      determine a first image from the endoscopic imaging system;
      determine, using the first image, that a first condition is present;
      determine a first response action to implement using the first endoscopic device;
      determine that a confidence score indicative of a likelihood that the first response action is a correct action is less than an automated action threshold;
      in response to determining the confidence score, generate a recommendation notification for the first response action comprising a request for manual approval of the first response action; and
      cause the first endoscopic device to implement the first response action.

* * * * *